United States Patent [19]

Garber et al.

[11] 4,025,618

[45] May 24, 1977

[54] METHOD FOR SEPARATION OF CRYOPRECIPITATE FROM BLOOD PLASMA

[75] Inventors: Jan W. Garber, Palatine; De Wayne G. Davisson, Mount Prospect, both of Ill.

[73] Assignee: Baxter Travenol Laboratories, Inc., Deerfield, Ill.

[22] Filed: Mar. 29, 1976

[21] Appl. No.: 671,515

Related U.S. Application Data

[62] Division of Ser. No. 503,018, Sept. 3, 1974, Pat. No. 3,986,506.

[52] U.S. Cl. .............................. 424/101; 424/177; 260/112 B
[51] Int. Cl.² ................ A61K 35/16; A61K 37/00; C07G 7/00
[58] Field of Search ................. 424/101, 177; 260/112 B

[56] References Cited

UNITED STATES PATENTS

| | | |
|---|---|---|
| 3,328,255 | 6/1967 | Ilg ........................................ 424/101 |
| 3,347,745 | 10/1967 | Rinfret et al. ........................ 424/101 |
| 3,607,858 | 9/1971 | Querry et al. ........................ 424/101 |

*Primary Examiner*—Sam Rosen
*Attorney, Agent, or Firm*—Paul C. Flattery; Garrettson Ellis

[57] ABSTRACT

A blood collection system which comprises several blood compatible sealed bags connected together by blood compatible conduits. Means for separating cryoprecipitate from blood plasma are provided. This separation is made by a filtering means. The filtering means is positioned in the outlet of one of the bags of the system. After the blood cells have been removed by a prior step, the remaining blood plasma is collected in the bag which has the filtering means in the outlet. In this bag, the blood plasma is frozen and then slowly thawed. Factor VIII rich cryoprecipitate forms in this bag as part of the freezing and thawing process. As the plasma melts, it flows from the bag through the filtering means. The filtering means positioned in the outlet of the bag retains the cryoprecipitate. Thus, the separation of Factor VIII rich cryoprecipitate from the blood plasma is effected.

10 Claims, 2 Drawing Figures

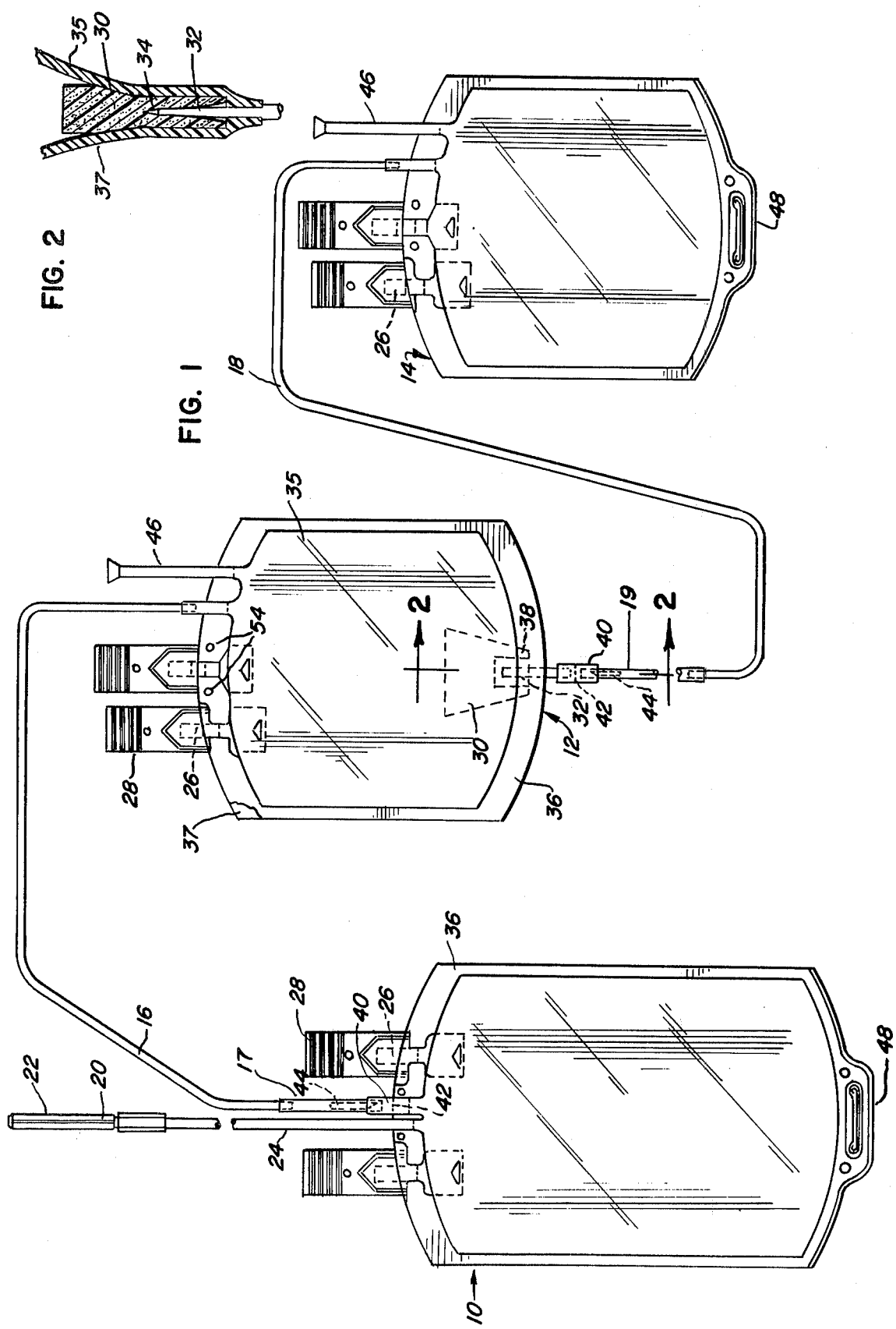

METHOD FOR SEPARATION OF CRYOPRECIPITATE FROM BLOOD PLASMA

This is a division of application Ser. No. 503,018, filed Sept. 3, 1974, now U.S. Pat. No. 3,986,506.

BACKGROUND OF THE INVENTION

This application relates to an improved blood collection apparatus and method in which the separation of Factor VIII rich cryoprecipitate from the remainder of the blood plasma is facilitated in an improved manner and in which the yield of Factor VIII rich cryoprecipitate is improved.

Many thousands of units of blood are collected each year in multiple bag blood collection systems comprising several blood compatible, sealed bags connected together with blood compatible tubing.

In a typical operation, a donor needle is inserted into the vein of a patient. This needle is connected by suitable tubing, such as vinyl tubing, to a first blood bag containing a small amount of conventional blood cell preservative, such as ACD or CPD. The blood is allowed to fill the first blood bag of the system, the donor needle is withdrawn from the patient, and the tubing connecting the needle to the bag is sealed. Following this, the blood collection system is centrifuged to cause the blood cells to settle and separate from the plasma. The plasma is then expressed through another tubing into a second blood bag, while the cells remain in the first blood bag.

Optionally, platelets may be harvested at this stage by a second centrifugation.

The plasma in the second blood bag is then frozen, either by refrigeration or by immersion in a mixture of dry ice and ethanol or a similar solvent.

After this, the frozen plasma is conventionally allowed to thaw slowly and then in centrifuged once again to settle solid material in the cold, thawed plasma. This solid material is known as Factor VIII rich cryoprecipitate.

After the conventional centrifuging, the plasma, which is now cryoprecipitate-poor, is expressed through tubing into a third blood bag for use, leaving behind the Factor VIII rich cryoprecipitate. This Factor VIII rich cryoprecipitate is the source of an important therapeutic agent for arresting the symptoms of a common type of hemophilia.

In accordance with this invention, an apparatus and a method of using the same is provided which permits the collection of increased yields of Factor VIII rich cryoprecipitate without the use of a second centrifuging step and which provides substantial savings in time and effort when compared with the present technique for obtaining Factor VIII rich cryoprecipitate.

DESCRIPTION OF THE INVENTION

This improved blood collection system incorporates a plurality of blood compatible, sealed bags connected together with blood compatible conduit means. Blood collection means, such as a phlebotomy needle connected to vinyl plastic tubing, communicates with the interior of the first of the bags. Accordingly, the blood is collected into the first bag and centrifuged to remove blood cells. The plasma is then expressed through the appropriate connecting conduit from the first bag to the second bag. Optionally, platelets may be harvested by another centrifugation in which the platelets remain in the second bag and the plasma is passed on to an additional bag. The bag containing the plasma is sealed, typically by heat sealing or clamping of the conduit, and frozen to form the Factor VIII rich cryoprecipitate.

For the final separation step, it is preferred to allow the frozen plasma to thaw slowly, permitting the thawed plasma to pass through the filtering means and out of the bag into another storage container as it melts. The thawing process typically can be performed between 2° and 20° C. (preferably between 2°–5° C.) for maximum yield of cryoprecipitate. The frozen bag is hung up and allowed to slowly melt and drain through the filtering means and bag outlet into another container. The thawing and draining process takes approximately 18 to 24 hours at 5° C. in a Fenwal blood bag containing one unit of blood plasma.

After the drainage is completed, the bag containing the Factor VIII rich cryoprecipitate can be sealed and separated from any remaining attached bags. One unit of cryoprecipiate is obtained (often with an increased yield of Factor VIII). Likewise, one unit of cryoprecipitate-poor plasma passes into the storage receptacle, which is usually the third or fourth bag of the system.

The filtering means used in the separation of the cryoprecipitate from the plasma must exhibit certain characteristics. It must pass the cryoprecipitate-poor plasma while retaining the Factor VIII rich cryoprecipitate. Cryoprecipitate-poor plasma can pass through a conventional screen type or membrane filter with a 2 micron pore. However, the cryoprecipitate clogs present-day screen or membrane filters. Therefore, part of the multiple blood bag system must account for and solve the clogging problem. Accordingly, "filtering means" as used herein means a filter which can pass the cryoprecipitate-poor plasma while retaining the Factor VIII rich cryoprecipitate and which solves the clogging problem.

Presently, the filtering means most effective in exhibiting these non-clogging properties is a depth filter. "A depth filter consists of fibrous, granular or sintered materials, pressed, wound, fired, or otherwise bonded into a tortuous maze of flow channels." (*Millipore's High Volume Pharmaceutical and Biological Filtration.* (1972) page 2.)

Because a depth filter is a three-dimensional irregular maze of material, it has a large internal surface area on which cryoprecipitate can be caught. Therefore, it will not readily become clogged as plasma is being passed through the filter.

Because a depth filter is a three dimensional maze of material, its filtering capacity cannot be described in terms of the size of the particles it will pass. Rather, a depth filter's filtering capacity is defined experimentally in terms of the percentage of particles of a certain size which will pass through it. It follows that outside factors will affect the filtering rate of depth filters. Flow rate, pressure, and particle adhesives are three such factors.

The presently preferred filtering means used in the improved blood collection system of this invention is a polyurethane open cell foam depth filter.

The specific embodiment described below illustrates one exemplary means for embodying the invention of this application. A "triple" bag system is shown bearing some similarity to the currently available Fenwal triple bags, but other structures such as single, double, and quadruple bag systems may be used if desired, modified in accordance with this invention.

In the drawings:

FIG. 1 is a plan view of a triple bag blood collection system, utilizing the invention of this application, with a portion broken away for showing construction detail.

FIG. 2 is a sectional view taken along the line 2—2 of FIG. 1.

Referring to the drawings, a blood collection system is shown comprising blood compatible, sealed blood bags 10, 12, 14, connected together with blood compatible conduit means 16, 18, which are shown to be vinyl plastic tubes. As stated above, many of the overall specific details of design of bags 10, 12, 14, and their respective conduits 16, 18, are well known, and similar bags made of vinyl plastic are commercially available at the present time.

A blood collection needle 20, conventionally sheathed with a needle protection cover 22, is shown to be connected in conventional manner by vinyl plastic tubing 24 to the interior of the first bag 10.

Vinyl plastic tubing 16 and flexible connector tube 17 provide communication between first bag 10 and second bag 12, while vinyl plastic tubing 18 and similar connector tube 19 provide connection between second bag 12 and third bag 14. Each of the three bags carries a pair of outlet ports 26 which are surrounded with conventional rupturable sheaths 28, specifically shown to be the design presently utilized in the Fenwal blood bags.

In accordance with this invention, filtering means is located in the interior of second bag 12, being positioned to cover outlet port tube 32 of bag 12. Outlet port tube 32, which is generally made of plastic, in turn communicates through tube 18 with the interior of bag 14.

Filtering means 30 may be polyurethane open cell foam depth filter sold under the brand name Scott Felt by the Scott Paper Company.

This material is a thick, sheet-like material, the grade specifically used herein being approximately ⅜ inch thick. The material, as originally made, has approximately 100 pores per inch, but then is compressed to ⅛ of its thickness, and heat set so that the material does not re-expand significantly after release from the compression.

Referring also to FIG. 2, a slit 34 is shown to be cut longitudinally in filtering means 30. Port tube 2 is positioned within the slit. Port tube 32 and filtering means 30 are positioned as shown in FIG. 1 between the pair of plastic sheets 35, 37 that makes up blood bag 12, and the periphery 36 of sheets 35, 37 is heat sealed together, with the bottom 38 of filtering means 30 between them, so that periphery 36, bottom 38 of fitlering means 30, and outlet port tube 32 all are sealed together into a unitary, sealed mass. Both ends of outlet port tube 32 protrude from opposite sides of the heat sealed periphery 36, for fluid communication therethrough.

Tube 19 is connected to port tube 32 by means of sleeve 40, which may be made of plastic or the like. Sleeve 40 defines a diaphragm 42 which blocks fluid flow out of bag 12 through port tube 32 until the diaphragm is ruptured by pointed tubular cannula 44, which is constructed in a manner similar to the diaphragm rupturing system of U.S. Pat. No. 3,110,308, and is retained in a bore of connector tube 19, since the bore of tube 18 is preferably too small to receive the cannula. Alternatively, the system for rupturing diaphragm 42 can be similar to U.S. Pat. No. 3,685,795, or any other conventional diaphragm rupturing system may be used.

A similar sleeve 40, having diaphragm 42, communicates with the interior of first blood bag 10, being retained with the corresponding heat sealed periphery 36 of bag 10 for leak free communication with the interior of the bag. Another hollow cannula 44, retained in connector tube 17, is present for the same function of opening diaphragm 42.

Sealed tubes 46 on bags 12 and 14 are ports used in the sterilization of the bags, to provide venting of the bags during and after the sterilization process. Thereafter the tubes are sealed as shown.

Identical serial numbers may be placed on vinyl tubing 16, 18 and 24 in the manner of Bellamy U.S. Pat. No. 2,896,619 for identification of the respective bags after they have been separated from each other, and for analysis of small samples of the contents of the bags.

Hangers 48 at the bottom of bags 10 and 14 permit inversion of the bags on an I.V. pole for conventional administration of the respective bag contents to a patient.

Accordingly, the triple bag blood collection system of FIG. 1 can be utilized by first obtaining a unit of fresh blood by conventional venipuncture with needle 20, and collection of a unit of blood into bag 10. Following such collection, donor tube 24 may be sealed by clamping, or by heat sealing in a HEMATRON heat sealing device, sold by the Fenwal division of Travenol Laboratories, Inc. Bag 10 contains a small amount of conventional blood cell preservative such as ACD or CPD preservative solution.

Following the blood collection, and sealing of tube 24, the blood bag system is centrifuged, to cause the blood cells in the sample to settle to the bottom of bag 10. After this has been accomplished, cannula 44 of bag 10 is moved forwardly to rupture diaphragm 42 by manual manipulation of flexible connector tube 17 to push cannula 44 through the diaphragm. The plasma can then be carefully expressed through tube 16 into the second bag 12, leaving the packed cells behind in bag 10.

Tube 16 is then usually severed after clamping or heat sealing, and bag 10 may be removed from the system, with its packed cells being preserved and stored in a conventional manner until needed for use.

The remaining bags of the system are then placed in a freezing environment, for example an ethanol-dry ice bath or mechanical refrigeration, to freeze the plasma in bag 12 to the solid state. After the plasma has solidly frozen, the cannula 44 associated with bag 12, and an appropriate portion of flexible connector tube 19, are warmed with the fingers or the like to permit the cannula to be advanced to rupture its associated membrane 42. This opens communication between bag 12 and tube 18. Bag 12 is then hung (if desired by means of holes 54) in a refrigerator at a temperature above the plasma freezing point. The preferred temperature is approximately 5° C. Bag 14 is placed at a positive vertically below bag 10 to receive cryoprecipitate-poor plasma, as the plasma melts, on a drop by drop basis. The melting plasma in bag 12 passes through filtering means 30 and outlet port tube 32, and accordingly through tubes 18 and 19 into bag 14.

After the plasma has thawed completely and has been filtered into bag 14, tube 18 may be sealed in a manner previously described, and severed to permit bag 14 and the cryoprecipitate-poor plasma to be removed for storage until needed for administration.

An abundant yield of Factor VIII rich cryoprecipitate remains captured on the filtering means 30 within bag 12. This material may be frozen for storage if desired.

When the cryoprecipitate is needed for use, it may be dissolved by adding about 10 cc. of sterile physiological saline solution, generally at room temperature, to the interior of bag 12. This may be done by opening one of the rupturable sheet closures 28 of bag 12 and inserting into the exposed outlet port 26 a medication injection site of the type currently sold by the Fenwal Division of Travenol Laboratories, Inc. The saline solution is then added through the medication injection site into the bag with a syringe and injection needle. The filtering means 30 is then manipulated and washed with the solution in the bag until all of the cryoprecipitate is dissolved in the solution. Thereafter, the bag is inverted so that the outlet ports 26 point downwardly, and the saline solution, with the dissolved cryoprecipitate, is withdrawn from the bag by means of the syringe needle.

Filtering means 30 is advantageously placed on the side of the bag opposite from the outlet port 26 used in this operation, since the bag may then be inverted with the outlet port pointed downwardly with the filtering means 30 out of contact with and above the liquid. The filtering means may then be manually squeezed to remove essentially all of the cryoprecipitate solution from it.

That which is claimed is:

1. In the method of blood collection which comprises passing blood plasma containing Factor VIII into a blood compatible, sealed container; freezing said blood plasma within said sealed container to cause the precipitation of Factor VIII-rich cryoprecipitate; and thawing said blood plasma, the improvement comprising passing the thawed blood plasma, under conditions to prevent the substantial redissolving of said cryoprecipitate, through filtering means, said filtering means comprising a depth filter made of open-celled foam, said depth filter being positioned within said container to obstruct an outlet therefrom, whereby cryoprecipitate-poor plasma is transferred from said container through said outlet, and said cryoprecipitate is retained on the filtering means within said container.

2. The method of claim 1 in which said open cell foam filter is made of polyurethane.

3. The method of claim 1 in which said frozen blood plasma is allowed to slowly thaw at a temperature below 20° C, while the plasma is allowed to pass through said filtering means promptly as it melts and out of said bag outlet.

4. The method of claim 1 in which said frozen blood plasma is allowed to thaw at 2°–5° C.

5. The method of claim 4 in which said open cell foam filter is made of polyurethane.

6. The method of claim 1 in which said cryoprecipitate-poor plasma is transferred to another blood-compatible sealed bag through a blood compatible conduit.

7. The method of claim 1 in which physiological saline solution is thereafter added to said second bag, to redissolve the cryoprecipitate, and said cryoprecipitate containing solution is thereafter removed from said second bag.

8. The method of claim 7 in which, after the cryoprecipitate is redissolved, any cryoprecipitate caught in the filter is removed from the filter.

9. The method of claim 8 in which the removal of cryoprecipitate from the filter is accomplished by washing the filter with a saline solution.

10. The method of claim 8 in which the removal of cryoprecipitate from the filter is accomplished by squeezing the filter.

* * * * *